United States Patent [19]

Wright, Jr. et al.

[11]  4,289,769
[45]  Sep. 15, 1981

[54] DERIVATIVES OF P-FORMYLBENZAMIDE AMIDINOHYDRAZONE AND USE THEREOF

[75] Inventors: William B. Wright, Jr., Woodcliff Lake; Andrew S. Tomcufcik, Old Tappan, both of N.J.

[73] Assignee: American Cyanamid Company, Stamford, Conn.

[21] Appl. No.: 176,233

[22] Filed: Aug. 8, 1980

[51] Int. Cl.$^3$ .............. A61K 31/165; A61K 31/535; C07C 133/12; C07D 295/18
[52] U.S. Cl. ..................... 424/248.56; 424/267; 424/274; 424/324; 544/162; 546/226; 564/149; 542/417; 260/326.5 E
[58] Field of Search ............ 544/162; 546/226; 260/326.5 E; 564/149; 542/417, 418; 424/248.56, 267, 274, 324

[56] References Cited

U.S. PATENT DOCUMENTS 3,655,560  4/1972  Andress ........................ 564/149
4,107,326  8/1978  Goldman et al. ............... 424/304

Primary Examiner—Henry R. Jiles
Assistant Examiner—R. W. Ramsuen
Attorney, Agent, or Firm—Edward A. Conroy, Jr.

[57] ABSTRACT

This disclosure describes novel derivatives of p-formylbenzamide amidinohydrazone and their use as hypotensive agents.

16 Claims, No Drawings

DERIVATIVES OF P-FORMYLBENZAMIDE AMIDINOHYDRAZONE AND USE THEREOF

BRIEF SUMMARY OF THE INVENTION

This invention relates to new organic compounds and, more particularly, is concerned with novel derivatives of p-formylbenzamide amidinohydrazone which may be represented by the following structural formula:

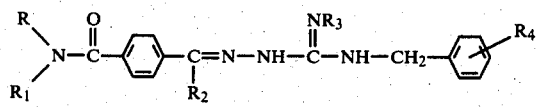

wherein R and $R_1$ may be the same or different and may be selected from hydrogen and alkyl ($C_1$–$C_6$), and where R and $R_1$ taken together with their associated nitrogen may be morpholine, piperidine and pyrrolidine; $R_2$ is hydrogen or methyl; $R_3$ is selected from the group comprising hydrogen, and lower alkyl ($C_1$–$C_3$); and $R_4$ may be hydrogen, lower alkyl ($C_1$–$C_3$), fluoro and chloro, the tautomers thereof and the pharmacologically acceptable acid-addition salts thereof.

DETAILED DESCRIPTION OF THE INVENTION

The novel compounds of the present invention are generally obtainable as white to pale yellow crystalline solids having characteristic melting points and absorption spectra. The bases are appreciably soluble in solvents such as acetone, ethanol, toluene, carbon tetrachloride, methylene chloride and the like but are relatively insoluble in water. The organic bases of the present invention form non-toxic acid-addition salts with a variety of pharmacologically acceptable organic and inorganic salt forming reagents. Thus, acid-addition salts, formed by admixture of the organic free base with one or two equivalents of an acid, suitably in a neutral solvent, are formed with such acids as sulfuric, phosphoric, hydrochloric, hydriodic, sulfamic, citric, lactic, fumaric, succinic, tartaric, acetic, benzoic, gluconic, ascorbic, and the like. The acid-addition salts are relatively insoluble in non-polar organic solvents such as diethyl ether, benzene, toluene, and the like but are appreciably soluble in water. For purposes of this invention, the free bases are equivalent to their non-toxic acid-addition salts.

The novel compounds of the present invention may be readily prepared in accordance with the following reaction scheme:

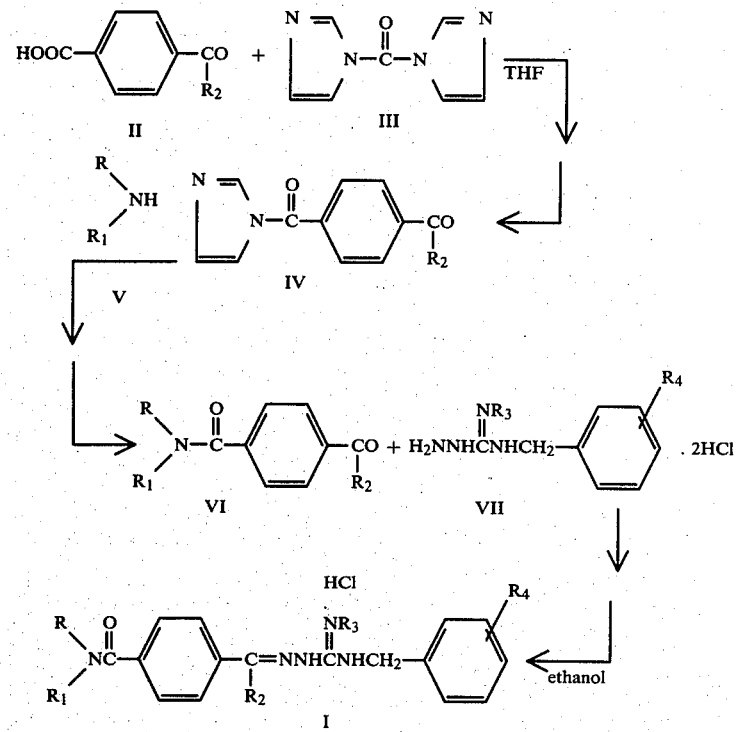

wherein R, $R_1$, $R_2$, $R_3$ and $R_4$ are as hereinabove defined. in accordance with the above reaction scheme, 4-carboxybenzaldehyde or 4-carboxyacetophenone II (0.1 mole) is mixed with N,N'-carbonyldiimidazole III (0.105 mole) in tetrahydrofuran and allowed to stand for one hour to give a solution of p-1-imidazolinylcarbonylbenzaldehyde or p-1-imidazolinylacetophenone IV. The appropriate amine V (0.12 mole) is added and the mixture is allowed to react at 25°–65° C. for one to 18 hours. The reaction mixture is diluted with water and concentrated to remove the solvent. The residue is extracted into methylene chloride, washed twice with water, with diluted hydrochloric acid, then with water, with diluted hydrochloric acid, then with water, dried over magnesium sulfate and concentrated. The crude p-formylbenzamide or p-acetylbenzamide compounds VI may be purified by recrystallization from solvents such as; hexane, ethyl acetate and the like or by partition chromatography.

A mixture of (0.015 mole) of the benzamide derivative VI and (0.015 mole) of the aminoguanidine derivative VII [prepared by the procedure of W. J. Finnegan, R. A. Henry and E. Lieber, J. Org. Chem. 18, 779 (1953) and generally used as the dihydrochloride salt] in 35 ml. of ethanol is heated at the reflux temperature for one to 2 hours. The reaction mixture is cooled, the desired product (I) is collected by filtration and washed with ether. If precipitation does not occur, an equal volume of ether is added and the procedure is repeated by trituration with ether and recrystallization from ethanol/ether.

The novel compounds of the present invention possess anti-hypertensive activity at non-toxic doses and as such are useful as hypotensive agents. The hypotensive properties of the compounds of the present invention have been shown when orally administered to mammals, specifically warm-blooded animals as described below.

The novel compounds of the present invention were tested for anti-hypertensive activity in procedure using spontaneously hypertensive rats (SHR) as follows: One male adult (16–20 weeks old) weighing about 300 grams SHR (Taconic Farms, Germantown, N.Y.) is dosed by gavage with the test compound at 100 mg./kg. with 0.9% sodium chloride loading at 25 ml./kg. at 0-hours. A second identical dose is given at 24 hours without saline loading and the mean arterial blood pressure (MABP) of the conscious rat is measured directly by femoral-iliac artery puncture at 28 hours. A 2nd or 3rd SH rat may be needed depending on the results of the 1st rat [Chan et al, Clinical and Experimental Hypertension, 1 (6), 817–830 (1979)]. The following representative compound of the present invention have been shown to possess anti-hypertensive activity when tested as described above.

1-p-Formylbenzoylpyrrolidine benzylamidinohydrazone hydrochloride 4-p-Formylbenzoylmorpholine benzylamidinohydrazone hydrochloride p-Formyl-N,N-dimethylbenzamide benzylamidinohydrazone hydrochloride N,N-Diethyl-p-formylbenzamide benzylamidinohydrazone hydrochloride 1-p-Formylbenzoylpiperidine benzylamidinohydrazone hydrochloride p-Formyl-N,N-dipropylbenzamide benzylamidinohydrazone hydrochloride p-Formyl-N-propylbenzamide benzylamidinohydrazone hydrochloride The novel compounds of the present invention have thus been found to be highly useful for lowering elevated blood pressure in mammals when administered in amounts ranging from about 1.0 milligrams to about 100.0 mg. per kilogram of body weight per day. A preferred dosage regimen for optimum results would be from about 15.0 mg. to about 35.0 per kilogram of body weight per day, and such dosage units are employed that a total of from about 1.0 gram to about 2.0 gram of active compound for a subject of about 70 kg. of body weight are administered in a 24 hour period. The dosage regimen may be adjusted to provide the optimum therapeutic response. For example, several divided doses may be administered daily or the dose may be proportionally reduced as indicated by the exigencies of the therapeutic situation. The compounds of this invention are preferably administered orally.

The compounds of the present invention may be administered as active components of compositions in unit dosage forms such as tablets, troches, pills, capsules, powders, granules, oral solutions or suspensions and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in this specification, these being features of the present invention.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For preparing solid compositions such as tablets or pills for oral therapeutic administration, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both, A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. Such compositions and preparations should contain at least 0.1% of active compound. The percentage of the compositions and preparations may, of course, be varied and may conveniently be between about 2% and about 60% of the weight of the unit. The amount of active compound in such therapeutically useful compositions is such that a suitable dosage will be obtained.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The invention will be described in greater detail in conjunction with the following specific examples.

EXAMPLE 1

1-p-Formylbenzoylpyrrolidine benzylamidinohydrazone hydrochloride

A mixture of 15 g. (0.1 mole) of 4-carboxybenzaldehyde, 17 g. (0.105 mole) of N,N'-carbonyldiimidazole and 150 ml. of tetrahydrofuran is allowed to stand at room temperature for one hour then 10 ml. (0.12 mole) of pyrrolidine is added. The reaction mixture is allowed to stand at room temperature for 16 hours and then heated in the steam bath for one hour. Water is added and the solvent is distilled off. The residue is extracted with methylene chloride, and the organic layer is washed with dilute hydrochloric acid and water, dried over magnesium sulfate and concentrated to an oil which gradually crystallizes. Recrystallization from hexane results in pure p-(1-pyrrolidinyl)carbonylbenzaldehyde, m.p. 60°–61° C.

A mixture of 50 g. of benzylaminoguanidine hydroiodide [W. J. Finnegan, R. A. Henry and E. Lieber, J. Org. Chem., 18, 779 (1953)] and 200 ml. of ethanol is stirred and 150 ml. of 3.5 N alcoholic hydrogen chloride is added. The reaction mixture is stirred for 2 hours longer, cooled and the benzylaminoguanidine dihydrochloride is collected by filtration, washed with cold ethanol, then ether and dried in a vacuum desiccator.

A mixture of 9.0 g. of p-(1-pyrrolidinyl)carbonylbenzaldehyde, 10.5 g. of benzylaminoguanidine dihydrochloride, and 100 ml. of ethanol is warmed for 2 hours, then is cooled. The product is collected by filtration, washed with a little ethanol and then ether, and dried in vacuo to yield 11.1 g. of the desired product as white crystals, m. p. 230°–233° C.

EXAMPLE 2

1-p-Formylbenzoylpyrrolidine-p-chlorobenzylamidinohydrazone hydrochloride

The above compound is obtained when p-chlorobenzylaminoguanidine dihydrochloride is substituted for benzylaminoguanidine dihydrochloride in the procedure of Example 1.

EXAMPLE 3

1-p-Formylbenzoylpyrrolidino-p-fluorobenzylamidinohydrazone hydrochloride

When p-fluorobenzylaminoguanidine dihydrochloride is substituted for benzylaminoguanidine dihydrochloride in the procedure of Example 1, the above compound is obtained.

EXAMPLE 4

4-p-Formylbenzoylmorpholine benzylamidinohydrazone hydrochloride

When morpholine is substituted for pyrrolidine in the procedure of Example 1, p-morpholinocarbonylbenzaldehyde, m.p. 87°–89° C. is first obtained. Reaction of this compound with benzylaminoguanidine dihydrochloride yields 4-p-formylbenzoylmorpholine benzylamidinohydrazone hydrochloride, as white crystals, m.p. 222°–225° C.

EXAMPLE 5

1-p-Formylbenzoylpyrrolidine α-methylbenzylamidinohydrazone hydrochloride

When 4-carboxyacetophenone is substituted for 4-carboxybenzaldehyde in the procedure of Example 1, p-(1-pyrrolidinyl)carbonylacetophenone is first obtained. When this compound is reacted with benzylaminoguanidine dihydrochloride, the product obtained is 1-p-formylbenzoylpyrrolidine α-methylbenzylamidinohydrazone hydrochloride.

EXAMPLE 6 p-Formyl-N,N-dimethylbenzamide benzylamidinohydrazone hydrochloride

A mixture of 15.0 g. of 4-carboxybenzaldehyde, 17.0 g. of N,N'-carbonyldiimidazole and 150 ml. of tetrahydrofuran is allowed to stand at room temperature for one hour. Dimethylamine is passed thru the above solution for one hour and the reaction mixture is allowed to stand at room temperature for 18 hours, then is heated at reflux temperature for one hour. Water is added and the solvent is distilled off. The residue is extracted with methylenechloride. The organic layer is washed with dilute hydrochloric acid and water, dried over magnesium sulfate and concentrated to an oil. The oil is triturated with a little methylene chloride and the insoluble material is filtered off. The mother liquor is concentrated and 7.9 g. of p-formyl-N,N-dimethylbenzamide is obtained as an oil.

A mixture of 2.66 g. of the above oil, 3.56 g. of benzylaminoguanidine dihydrochloride and 35 ml. of ethanol is heated for two hours then is diluted with ether. The precipitate which separates is collected by filtration and is recrystallized from ethanol/ether to give the product of the Example as white crystals, m.p. 198°–202° C.

EXAMPLE 7

N,N-Diethyl-p-formylbenzamide benzylamidinohydrazone hydrochloride

When diethylamine is substituted for dimethyl amine in the procedure of Example 6, N,N-diethyl-p-formyl benzamide is obtained as an oil. When this oil is reacted with benzylaminoguanidine dihydrochloride, the product of the Example is obtained as cream colored crystals, m.p. 218°–221° C.

EXAMPLE 8 p-Formyl-N,N-dimethylbenzamide p-tolylamidinohydrazone hydrochloride

As for Example 6 when p-tolylaminoguanidine dihydrochloride is reacted with p-formyl-N,N-dimethylbenzamide the product of the Example is obtained.

EXAMPLE 9

1-p-Formylbenzoylpyrrolidine 1-benzyl-2-ethylamidinohydrazone hydroiodide

A mixture of 9.0 g. of p-(1-pyrrolidinyl)carbonyl benzaldehyde, 10.0 g. of 1-amino-2-benzyl-3-ethylguanidine hydroiodide [U.S. Pat. No. 4,107,326 (1978)] and 50 ml. of ethanol is warmed for 2 hours, the mixture is cooled to separate the product of the example which is collected by filtration.

EXAMPLE 10

N,N-Diethyl-p-formylbenzamide 1-benzyl-2-methylamidinohydrazone hydroiodide

When a mixture of 9.0 g. of 1-amino-2-benzyl-3-methylguanidine hydroiodide [W. J. Finnegan, R. A. Henry and E. Lieber, J. Org. Chem., 18, 779 (1953)], 10.0 g. of N,N-diethyl-p-formylbenzamide and 50 ml. of ethanol is warmed for 2 hours and cooled the product of the Example is obtained.

EXAMPLE 11

1-p-Formylbenzoylpiperidine benzylamidinohydrazone hydrochloride

A mixture of 12.0 g. of 4-carboxybenzaldehyde, 13.6 g. of N,N'-carbonyldiimidazole and 100 ml. of tetrahydrofuran is allowed to stand for one hour, then 9.4 ml. of piperidine is added. The reaction mixture is allowed to stand for 18 hours, then heated at reflux temperature for one hour. Water is added and the solvent is distilled off. Methylene chloride is added and the solution is washed with 25 ml. of concentrated hydrochloric acid, then with water then is dried over magnesium sulfate. The mother liquor is concentrated to yield p-piperidinocarbonylbenzaldehyde as an oil.

A mixture of 1.52 g. of the above oil, 1.66 g. of benzylaminoguanidine dihydrochloride and 15 ml. of ethanol is heated at reflux temperature for 1½ hours and diluted with a little ether. The resulting mixture is filtered to obtain 2.6 g. of the desired product as white crystals, m.p. 182°-185° C.

EXAMPLE 12

1-p-Formylbenzoylpiperidine m-chlorobenzylamidinohydrazone hydrochloride

When m-chlorobenzylaminoguanidine dihydrochloride is substituted for benzylaminoguanidine dihydrochloride in the procedure of Example 11, the desired product is obtained.

EXAMPLE 13 p-Formyl-N,N-dipropylbenzamide benzylamidinohydrazone hydrochloride

When dipropylamine is substituted for pyrrolidine in the procedure of Example 1, the product of the Example is obtained as white crystals, m.p. 190°-192° C.

EXAMPLE 14 p-Formyl-N,N-dimethylbenzamide o-fluorobenzylamidinohydrazone hydrochloride

When o-fluorobenzylaminoguanidine dihydrochloride is substituted for benzylaminoguanidine dihydrochloride in the procedure of Example 6, the desired product is obtained.

EXAMPLE 15 p-Formyl-N-propylbenzamide benzylamidinohydrazone hydrochloride

A mixture of 15.0 g. of 4-carboxybenzaldehyde, 17.0 g. of N,N'-carbonyldiimidazole and 100 ml. of tetrahydrofuran is allowed to stand at room temperature for 3 hours, then 9.8 ml. of N-propylamine are added. The reaction mixture is allowed to stand at room temperature for 18 hours and is then heated at reflux temperature for one hour, diluted with water and concentrated. The oil which separates is washed twice with water and then purified by partition chromatography to yield p-formyl-N-propylbenzamide, m.p. 71°-74° C.

A mixture of 5.7 g. of p-formyl-N-propylbenzamide, 7.1 g. of benzylaminoguanidine dihydrochloride and 100 ml. of ethanol is heated for two hours and cooled. The precipitate is collected by filtration to give the desired product as white crystals, m.p. 233°-235° C.

We claim:

1. A compound selected from the group consisting of those of the formula:

$$\underset{R_1}{\overset{R}{\diagup}}N-\overset{O}{\overset{\|}{C}}-\underset{}{\underset{}{\bigcirc}}-\underset{R_2}{\overset{}{C}}=N-NH-\overset{NR_3}{\overset{\|}{C}}-NH-CH_2-\underset{}{\bigcirc}-R_4$$

wherein R and $R_1$ may be the same or different and may be selected from hydrogen and alkyl ($C_1$-$C_6$), and where R and $R_1$ taken together with their associated nitrogen may be morpholine, piperidine and pyrrolidine; $R_2$ is hydrogen or methyl; $R_3$ is selected from the group comprising hydrogen, and lower alkyl ($C_1$-$C_3$); and $R_4$ may be hydrogen, lower alkyl ($C_1$-$C_3$), fluoro and chloro, the tautomers thereof and the pharmacologically acceptable acid-addition salts thereof.

2. The compound according to claim 1, 1-p-formylbenzoylpyrrolidine benzylamidinohydrazone hydrochloride.

3. The compound according to claim 1, 4-p-formylbenzoylmorpholine benzylamidinohydrazone hydrochloride.

4. The compound according to claim 1, p-formyl-N,N-dimethylbenzamide benzylamidinohydrazone hydrochloride.

5. The compound according to claim 1, N,N-diethyl-p-formylbenzamide benzylamidinohydrazone hydrochloride.

6. The compound according to claim 1, 1-p-formylbenzoylpiperidine benzylamidinohydrazone hydrochloride.

7. The compound according to claim 1, p-formyl-N,N-dipropylbenzamide benzylamidinohydrazone hydrochloride.

8. The compound according to claim 1, p-formyl-N-propylbenzamide benzylamidinohydrazone hydrochloride.

9. The method of lowering elevated blood pressure in a mammal which comprises administering internally to said mammal an effective amount of a compound selected from the group consisting of those of the formula:

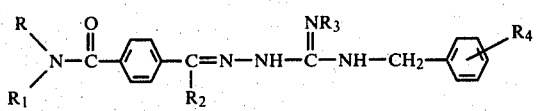

wherein R and $R_1$ may be the same or different and may be selected from hydrogen and alkyl ($C_1$–$C_6$), and where R and $R_1$ taken together with their associated nitrogen may be morpholine, piperidine and pyrrolidine; $R_2$ is hydrogen or methyl; $R_3$ is selected from the group comprising hydrogen, and lower alkyl ($C_1$–$C_3$); and $R_4$ may be hydrogen, lower alkyl ($C_1$–$C_3$), fluoro and chloro, the tautomers thereof and the pharmacologically acceptable acid-addition salts thereof.

10. The method according to claim 9, wherein the compound is 1-p-formylbenzoylpyrrolidine benzylamidinohydrazone hydrochloride.

11. The method according to claim 9, wherein the compound is 4-p-formylbenzoylmorpholine benzylamidinohydrazone hydrochloride.

12. The method according to claim 9, wherein the compound is p-formyl-N,N-dimethylbenzamide benzylamidinohydrazone hydrochloride.

13. The method according to claim 9, wherein the compound is N,N-diethyl-p-formylbenzamide benzylamidinohydrazone hydrochloride.

14. The method according to claim 9, wherein the compound is 1-p-formylbenzoylpiperidine benzylamidinohydrazone hydrochloride.

15. The method according to claim 9, wherein the compound is p-formyl-N,N-dipropylbenzamide benzylamidinohydrazone hydrochloride.

16. The method according to claim 9, wherein the compound is p-formyl-N-propylbenzamide benzylamidinohydrazone hydrochloride.

* * * * *